United States Patent
Miller et al.

(10) Patent No.: US 8,019,620 B2
(45) Date of Patent: Sep. 13, 2011

(54) SYSTEM AND METHOD FOR MEDICAL PRIVACY MANAGEMENT

(75) Inventors: Heather M. Miller, Kansas City, MO (US); Wayne E. Friesen, Olathe City, KS (US); John F. Travis, Kansas City, MO (US); Phillip E. Landry, Excelsior Springs, MO (US); Ryan J. McKenna, Pleasant Valley, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1378 days.

(21) Appl. No.: 11/025,996

(22) Filed: Jan. 3, 2005

(65) Prior Publication Data

US 2006/0155668 A1 Jul. 13, 2006

(51) Int. Cl.
G06Q 10/00 (2006.01)
G06Q 50/00 (2006.01)
A61B 5/00 (2006.01)
G06F 19/00 (2011.01)

(52) U.S. Cl. .............................................. 705/2; 705/3
(58) Field of Classification Search .................... 705/2–3
See application file for complete search history.

(56) References Cited

U.S. PATENT DOCUMENTS

| 6,804,787 B2 * | 10/2004 | Dick | 726/1 |
| 2001/0053986 A1 * | 12/2001 | Dick | 705/3 |
| 2002/0016923 A1 * | 2/2002 | Knaus et al. | 713/200 |

FOREIGN PATENT DOCUMENTS

WO  WO 2004102393 A1 * 11/2004

* cited by examiner

*Primary Examiner* — Luke Gilligan
*Assistant Examiner* — Joy Chng
(74) *Attorney, Agent, or Firm* — Shook, Hardy & Bacon L.L.P.

(57) ABSTRACT

A system and related techniques provide an integrated platform for privacy management of electronic medical records, encompassing the entire life cycle of privacy management including the capture of patient consents and other privacy status information, request management to receive and filter requests by health insurance companies and others, publishing management and release management of the contents of the electronic medical record. According to embodiments of the invention in one regard, various modules and logic may directly access the patient EMR and extract appropriate segments of information called for by validated requests, to publish that information as well as record or log that access history. The invention may thus provide an integrated tool to document compliance with HIPAA and other regulatory requirements. According to embodiments of the invention in another regard, medical information requests and other transactions which were originally made in paper or hard-copy form may likewise be assimilated into the access database, along with release requests which are electronic in nature.

15 Claims, 4 Drawing Sheets

SYSTEM AND METHOD FOR MEDICAL PRIVACY MANAGEMENT

CROSS-REFERENCE TO RELATED APPLICATION

Not applicable.

STATEMENT REGARDING FEDERALLY SPONSORED RESEARCH OR DEVELOPMENT

Not applicable.

FIELD OF THE INVENTION

The invention relates to the field of healthcare information management, and more particularly to a system and method to manage the privacy of legally protected medical information.

BACKGROUND OF THE INVENTION

The Health Information Portability and Accountability Act of 1996 (HIPAA) and other legal mandates have heightened the safeguards protecting patient privacy and medical confidentiality in many regards. Healthcare information management (HIM) professionals are now confronted with an array of procedural and substantive requirements which have been put in place to ensure that a person's medical condition or records are not inappropriately disclosed to third parties. In response to those and other compliance requirements, various information technology platforms have been deployed with a goal of managing patient records and privacy.

Much of the task of medical privacy management revolves around protecting access to, and recording disclosure activity from, the patient's electronic medical record (EMR). Certain commercial platforms have been deployed which automate or assist in the task of medical record publishing or dissemination from the EMR as one task, and request management in the sense of documenting release of information (ROI) requests by health insurers and others as another. Patient consent capture and archiving information requests which are made not for release of an EMR, but other purposes, form other tasks which HIM managers must manage on a day to day basis in hospitals and other medical facilities.

However, such privacy management tools as exist do not permit an information manager to completely monitor and archive the whole privacy life cycle including receiving and conditioning medical information based on legal guidelines, capturing the set of patient consents that surround that information, managing release requests made for that information, tracking medical record publishing activity when a release is validated and also tracking ancillary or non-release requests, as well. Since no integrated platform exists which can manage all such access and publishing functions, nor to further integrate the tracking of paper information release versus electronic publishing, HIM managers are left with the less satisfactory choice of operating multiple platforms to accomplish the array of necessary tasks. In another regard, managers and facilities which lack even partial information tools must also manually record paper requests and other hardcopy activity which, is not or can not be reflected in or stored by electronic media. Other problems in healthcare information technology and privacy management exist.

SUMMARY OF THE INVENTION

The invention overcoming these and other problems in the art relates in one regard to a system and method for medical privacy management, in which an information platform may be deployed with logic to manage multiple privacy management phases, including patient consent capture, request management, publishing and release of electronic medical records or other sensitive or protected data. According to embodiments of the invention in one regard, the privacy management platform including those control or logic modules may directly access the patient's EMR or other clinical or medical record itself to support and fulfill publishing and other requests. Among advantages of the invention in one regard, the privacy management platform may therefore permit an HIM or other manager to track, manage and verify privacy compliance activity with respect to any patient requested or provider policy based restrictions on disclosure of medical information, and perform formerly diverse actions within one integrated tool, without a need to close or switch applications or databases. In addition, the integrated nature of the privacy management platform of the invention may permit the annotation or marking of a release or other request as being complete or in another status, as part of the workflow so that the life cycle of release activity may be documented and logged for auditing and other purposes. According to embodiments of the invention in a further regard, the inventive privacy management platform may also assimilate the record keeping of paper copy requests for release and other requests, which may or may not involve original electronic records or communications.

BRIEF DESCRIPTION OF THE DRAWINGS

The invention will be described with reference to the accompanying drawings, in which like numerals reference like elements and in which.

DETAILED DESCRIPTION OF EMBODIMENTS

Figure 1:
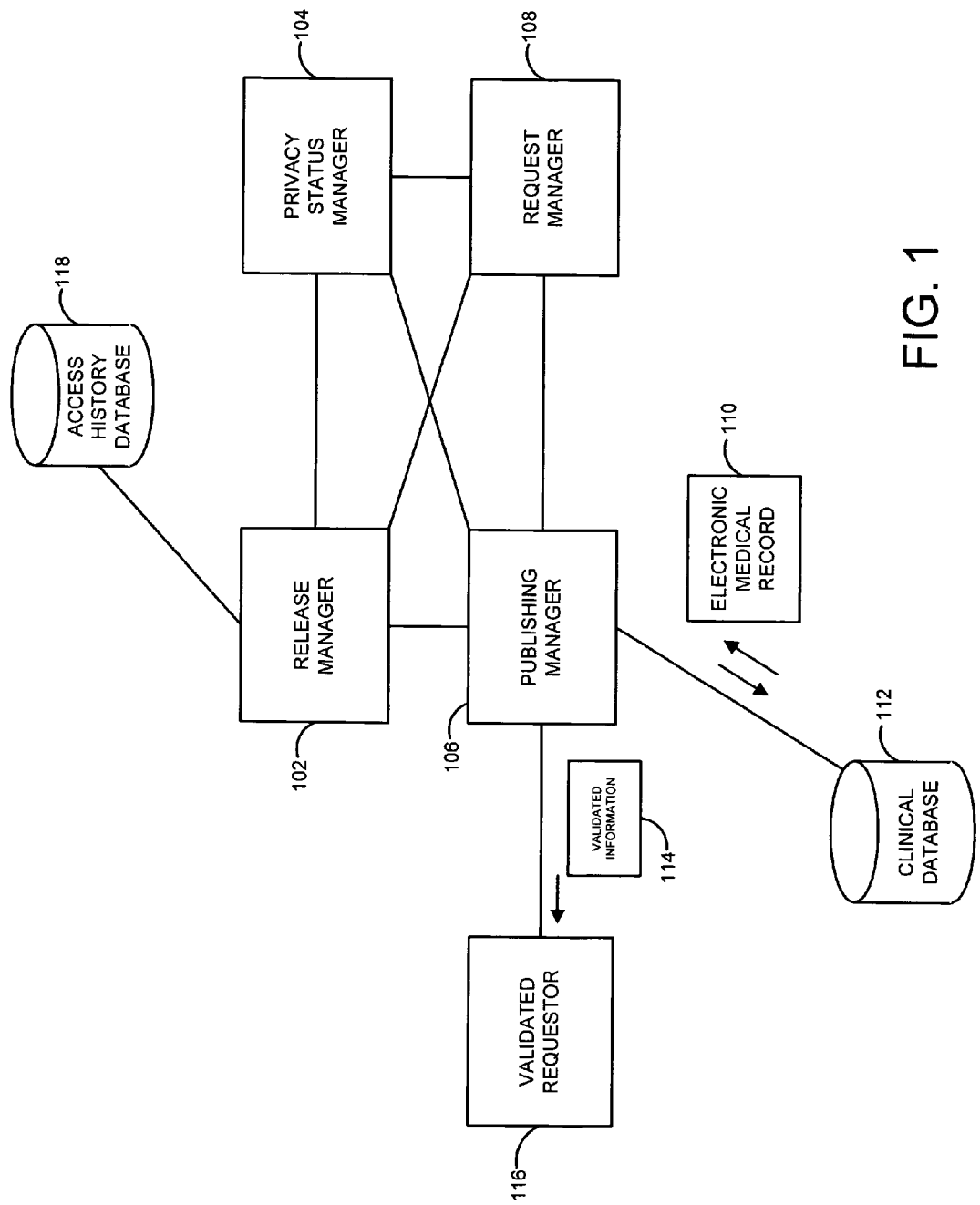
FIG. 1 illustrates an overall architecture of a system for medical privacy management, according to embodiments of the invention.

FIG. 1 illustrates an architecture in which a system and method for medical privacy management may operate, according to embodiments of the invention. As illustrated in that figure, a medical information platform according to the invention may be, include or interface to privacy management logic or control which includes or hosts a set of functional control modules, managers or engines. Those resources as illustrated may include a release manager 102, a privacy status manager 104, a publishing manager 106 and a request manager 108. Each of those resources may in embodiments communicate with each other, and with storage media including a clinical database 112 which may store an electronic medical record 110 for a patient or group of patients, including various medical history, clinical diagnosis, patient chart, pharmaceutical prescription and other information. According to embodiments of the invention in one regard, some portions or all of the clinical information contained in electronic medical record 110 or other objects or files may enjoy legally protected status under HIPAA or other legal or other guidelines, which may require the safeguarding and documentation of disclosure of that content on privacy grounds.

According to embodiments of the invention in one regard, in operation as shown, a requesting party may make a request for access to, and/or extraction of data from, a patient's electronic medical record 110. The requesting party may be or include, for example, a health insurance company or organization, a federal or state health agency or body such as the Centers for Medicare and Medicaid Services (CMS), physicians for instance for clinical purposes, from private individuals or other entities. The request may be received electronically by request manager 108. In further embodiments, the request may be received via paper copy or other hard copy or media, and for example scanned in or typed or entered in electronic form, via request manager 108.

The request manager 108 may receive the request, and make a determination whether the requesting party has valid standing or interest to propose the information request, for instance by identifying patient healthcare account numbers or identifiers, or otherwise. Upon validation, the request manager 108 may communicate with the privacy status manager 104, to determine the privacy status of the subject patient's electronic medical record 110 or other requested information. According to embodiments of the invention in one regard, the privacy status manager 104 may determine whether the patient has recorded valid consents or authorizations for one or more types of information access or release. For example, the patient may have recorded their consent to release surgical or clinical records for the last five years, or other period, or their consent to limited or unlimited consent to release of DNA typing. The patient illustratively on the other hand may have declined to consent to release information related to pregnancy status, drug or alcohol rehabilitation treatment, or treatment for sexually transmitted or chronic diseases. Other classes, types and categories of consents or authorizations are possible.

The request manager 108 may determine that the pending request is for a valid type or component of information in the patient's electronic medical record 110, and communicate with the publishing manager 106 in that case. The publishing manager 106 may in embodiments communicate directly, or indirectly with clinical database 112 to access the patient electronic medical record 110, for instance identifying the record by patient name, social security number, or other identifier, which may in embodiments be secure or encrypted. The information correlated to the validated requestor's request may then be extracted as validated information 114 to the publishing manager 106. The publishing manager 106 may then transmit, copy or otherwise communicate the validated information 114 to the validated requestor 116, for instance via the Internet, an intranet, or other network or channel, which in embodiments may likewise be secure or encrypted.

Before, simultaneously with, or after the release or dissemination of the validated information 114 to the validated requestor 116, the publishing manager 106 may communicate with release manager 102 to document and record the publishing or accessing event. The release manager 102 may, for example, mark or annotate the status of the pending request, including to indicate the request is received, denied or rejected, in process, or complete. That status and related information may in one regard be stored to an access history database 118, for instance to record a log, audit trail or other record or history of the request and publishing cycle for protected information stored in the electronic medical record 110 or other object or store. According to embodiments of the invention in one regard, an HIM or other manager may therefore access an automatically built, integrated data record of that processing cycle without resort to other tools or platforms. According to embodiments of the invention in another regard, again paper or other hard copy or other requests may likewise be scanned, entered or incorporated into access history database 118, or other privacy records. According to embodiments of the invention in a yet further regard, other types of request which may be made for data not directly stored in, dependent on or related to the electronic medical record 110, or not comparably protected under HIPAA or other regulations, may likewise be managed and documented, for instance requests for patient address or demographic information, healthcare insurance provider information, or other data or information related to the patient, or otherwise.

Figure 2:
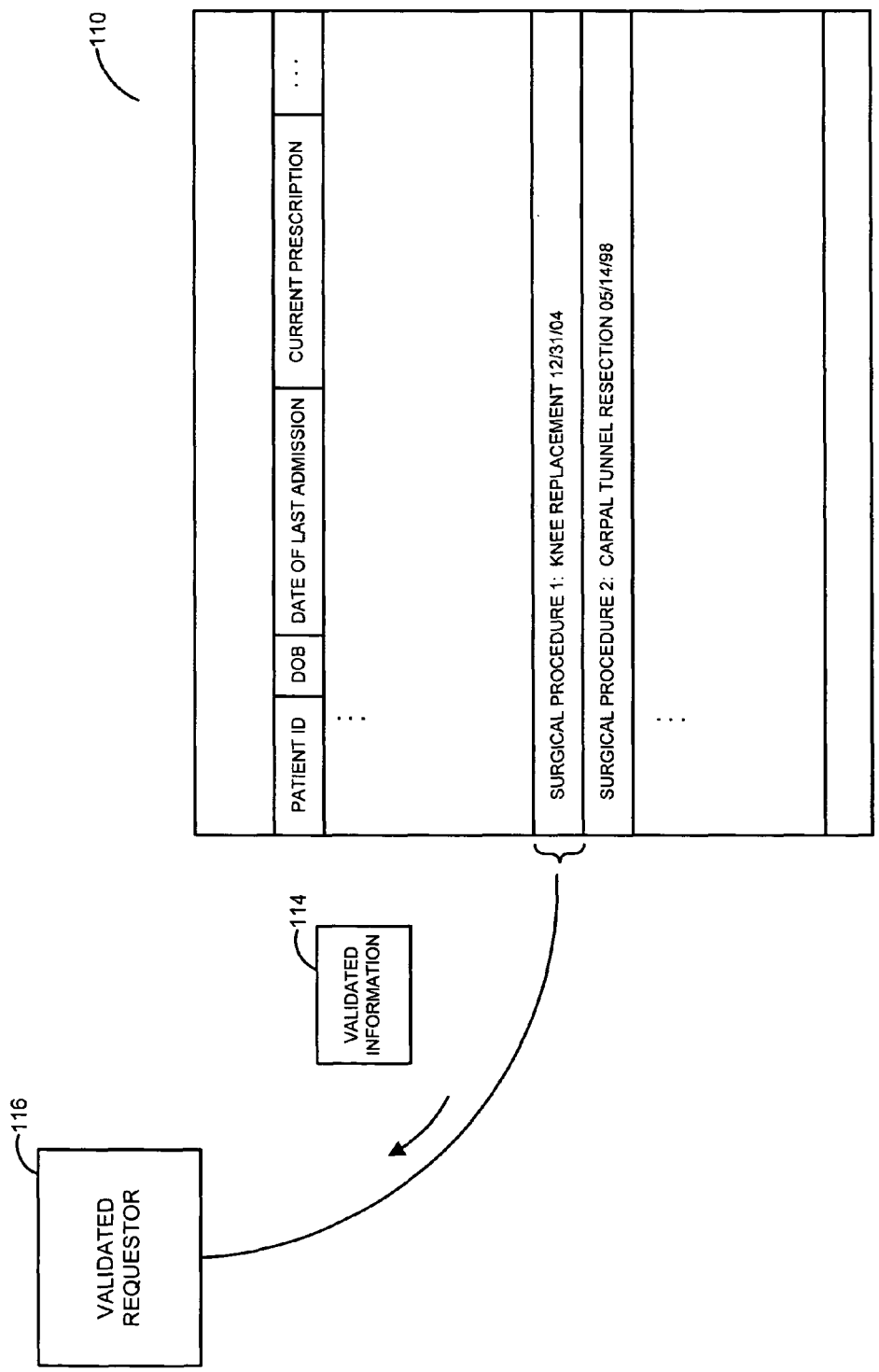
FIG. 2 illustrates an access operation on an electronic medical record, according to embodiments of the invention.

According to embodiments, the end to end privacy management platform may therefore receive, process and fulfill the request for and dissemination of selected information in an electronic medical record 110, for valid clinical, insurance or other purposes. Thus, and as for example illustrated in FIG. 2, the privacy management logic of the invention may directly or indirectly access the electronic medical record 110 to identify and extract validated information 114 for delivery to the validated requestor 116, in a controlled and comprehensive fashion including necessary privacy compliance. In embodiments as shown in that figure, the request may seek specific or defined information or classes of information, for instance data regarding a patient's operative procedures or records for the last year.

In other cases, requests may be made in connection with defined categories of requests such as employment or life insurance, which may entail specific limitations on the extracted data or require specific consents or authorizations from the patient. In the case of such a request as shown, appropriate data fields corresponding to that targeted request and forming validated information 114, for instance illustratively documenting a knee replacement or other surgical procedure or event, may therefore be identified, extracted and transmitted to a validated requestor 116 in a continuous and cohesive workflow, with automatic recording of necessary HIPAA or other privacy auditing information, while protecting remaining information from unrequested, unauthorized or otherwise noncompliant disclosure.

According to embodiments of the invention in one regard, the access and disclosure history stored to access history database 118 may be stored for specified intervals such as five or ten years, or archived or indefinitely stored. The privacy status information based in part upon which publishing or dissemination activity may occur, may likewise be stored, recorded or held in force for specified intervals, or indefinitely. Thus for example specific patient disclosure consents or authorizations may be stored or effective for a period for instance of years, or maintained in force indefinitely or permanently, or until amendment by the patient or other legitimate entity.

Figure 3:
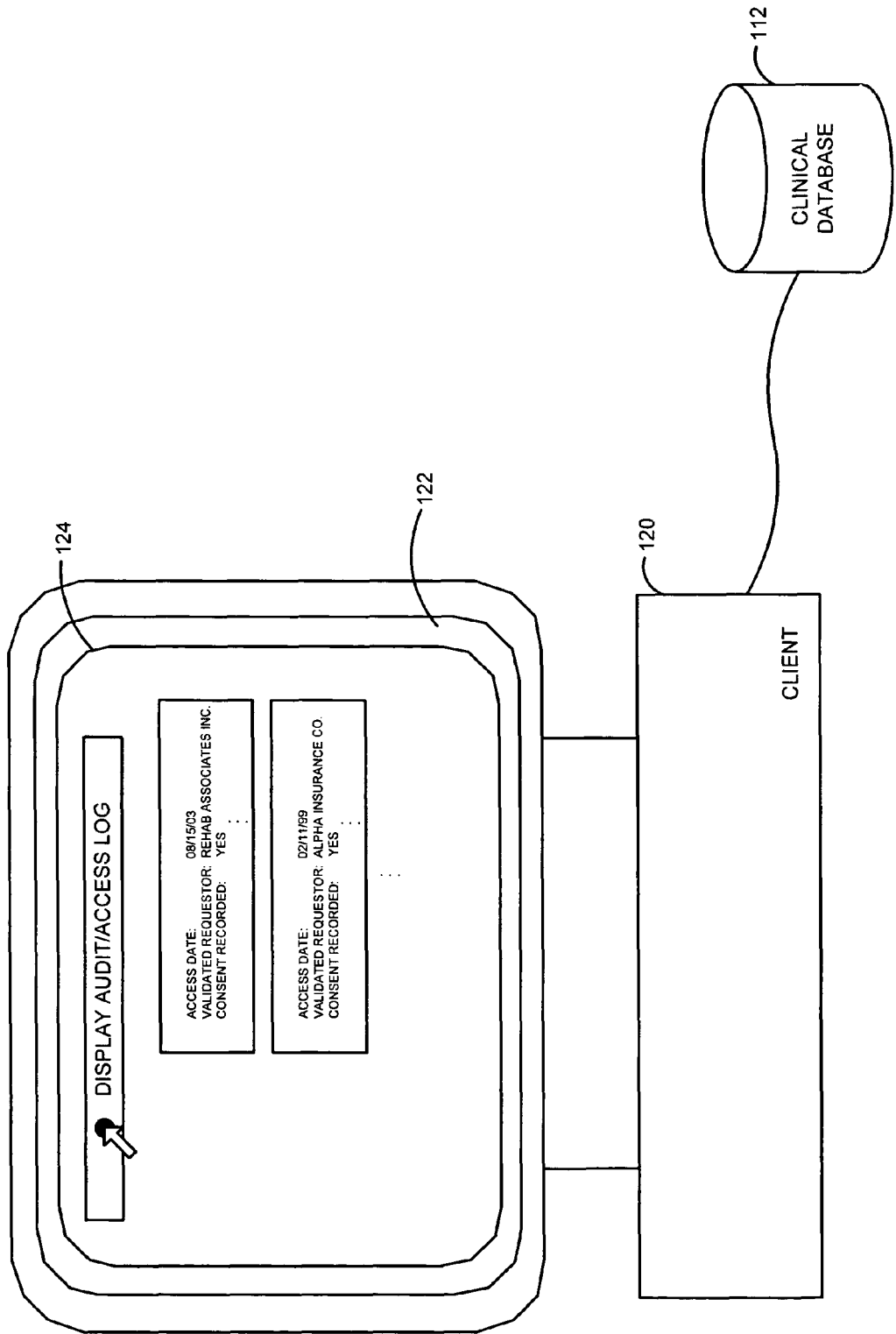
FIG. 3 illustrates a user interface by which a privacy medical system may be accessed, according to embodiments of the invention.

According to embodiments of the invention in a further regard, the privacy management logic including release manager 102, privacy status manager 104, publishing manager 106 and request manager 108 or other engines or modules may each be hosted or accessed by, or executed in a client such as a desktop, mobile or computer or other machine or resource. According to embodiments of the invention in that regard, and as for instance illustrated in FIG. 3, an HIM manager or other manager or supervisor may operate a client 120 for instance using a user interface 122 such as a graphical user interface, to access, initiate or manipulate the privacy management controls of the invention. In embodiments as shown, the client 102 may communicate with the clinical database 112 to directly or indirectly access the clinical database 112 to access electronic medical record 110 and other clinically related data, and may operate a privacy management user interface 124 in doing that. Privacy management user interface 124 may present an HIM or other manager with a set of objects, selectable options and other resources to view, review and document a patient's or others' privacy event history. Thus for example and as shown, the HIM or other user may access or manipulate the privacy management user interface 124 to access or communicate with access history database 118, and view the privacy disclosure history, log or record associated with a patient, illustratively including the date, purpose, requester and other descriptive data recorded for a publishing or disclosure event. According to embodiments of the invention in one regard, therefore, satisfactory documentation of consent and disclosure events may be integrated into the overall platform, including for HIPAA and other compliance.

Figure 4:
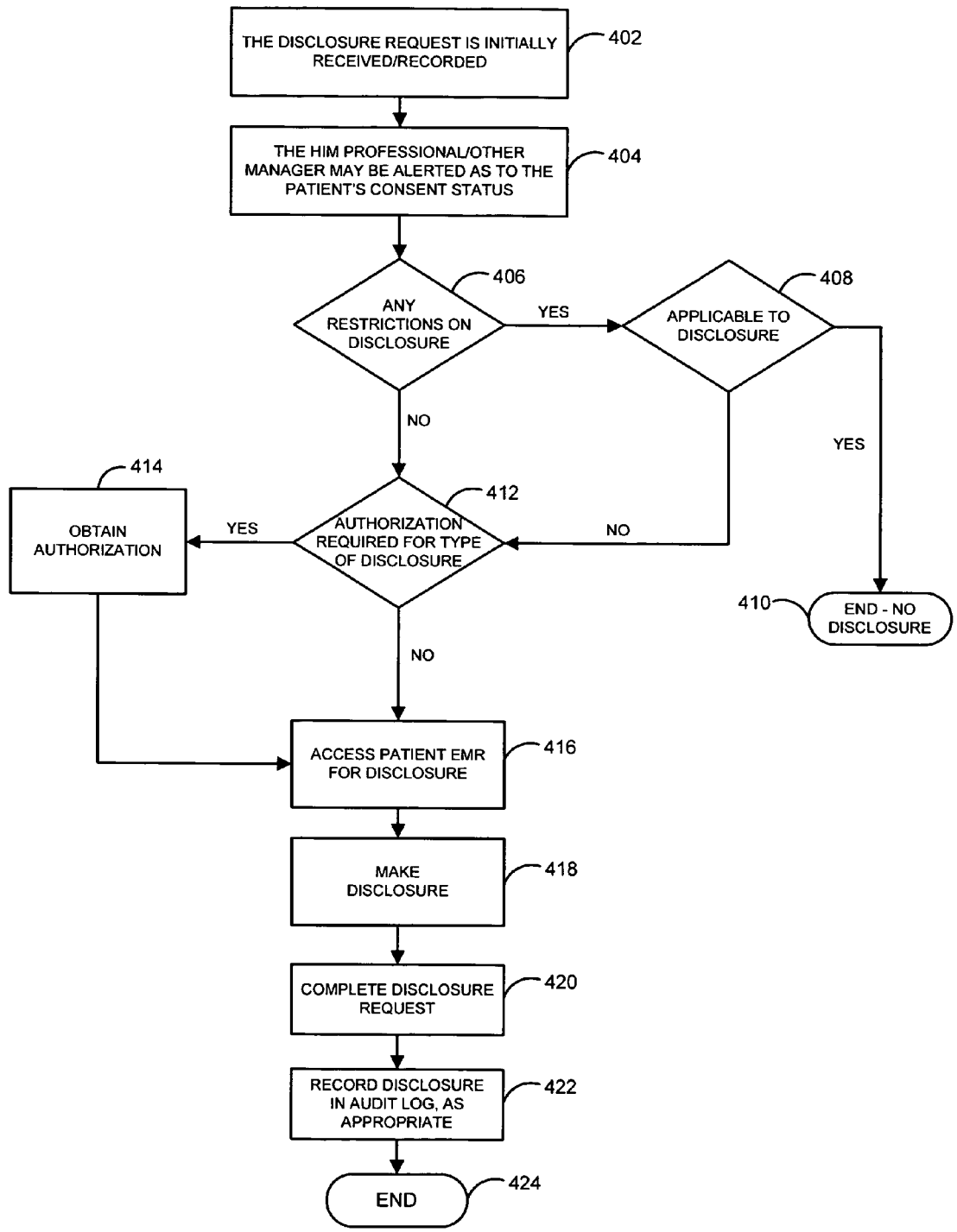
FIG. 4 illustrates a flowchart of overall privacy management processing, according to embodiments of the invention.

FIG. 4 illustrates overall privacy management processing, according to embodiments of the invention. In step 402, a disclosure request may be initially received and/or recorded, for instance via release manager 102. The disclosure request may be received from, for example, a healthcare insurance company, a federal or state health agency such as CMS, physicians for instance for clinical purposes, from private individuals or other entities. In step 404, an information manager such as an HIM or other manager or personnel may be alerted to the subject patient's privacy status, for instance via privacy status manager 104. In step 406, a determination may be made whether any restrictions on disclosure of or access to the patient's electronic medical record 110 or other data may be in place. If the determination is made in step 406 that a privacy or access restriction is in place, processing may proceed to step 408 in which a determination may be made whether the restriction is applicable to the pending request. If the determination is made in step 408 that the restriction applies to the request, processing may proceed to step 410 in which processing may end with a result of no disclosure being authorized or made.

If a determination is made in step 406 that no privacy or disclosure restrictions exist, processing may proceed to step 412. Similarly, if a determination is made in step 408 that no privacy or disclosure restrictions exist with respect to the requested information, processing may likewise proceed to step 412. In step 412, a determination may be made whether a specific authorization may be required for the particular type of disclosure being requested. If the determination in step 412 is that an authorization is required, processing may proceed to step 414 where authorization may be obtained, for instance via electronic signature or other communication with the patient, and after which processing may proceed to step 416. If the determination in step 412 is that no authorization is required, processing may likewise proceed to step 416. In step 416, the patient's electronic medical record 110 or other record or data may be accessed, for instance via publishing manager 106 to identify or extract validated information for disclosure from that source.

In step 418, the validated information 114 may be disclosed to the validated requester 116 or other entity, for instance via publishing manager 106. In step 420, the disclosure request may be completed and recorded as completed, for instance via release manager 102 or other logic. In step 422, the disclosure event may be recorded to access history database 118 as part of an audit log or other record, to provider for instance documentation for HIPAA or other regulatory or compliance purposes. In step 424, processing may repeat, return to a prior processing point, jump to a further processing point or end.

The foregoing description of the invention is illustrative, and modifications in configuration and implementation will occur to persons skilled in the art. For instance, while the invention has generally been described in terms of a platform which records medical information transactions to a single access history database 118, in embodiments the log or record of access and other activity may be stored to two or more local or remote databases or other data stores.

Similarly, while the invention has in embodiments been described as accessing an electronic medical record 110 from a single clinical database 112, in embodiments an EMR or other clinical data may be accessed or amalgamated from multiple local or remote sources or stores. Similarly, while the invention has in some cases been generally described as including privacy management logic or control which is broken down into modules or engines including release manager 102, privacy status manager 104, publishing manager 106 and request manager 108, in embodiments various control functions may be redistributed or shared between those or other modules or engines. Also, while the clinical database 112 and the access history database 118 have in embodiments been described as separate databases, in embodiments the clinical and access history data may be stored in a comprehensive, unified database. Other hardware, software or other resources described as singular may in embodiments be distributed, and similarly in embodiments resources described as distributed may be combined. Further, while in certain embodiments the invention has been described as involving privacy management logic which may be hosted on a single local client 102, in embodiments one or more manager or other functional control resources may be distributed to or divided between one or more remote or local machines, servers or other hardware or resources. The scope of the invention is accordingly intended to be limited only by the following claims.

We claim:

1. Computer-storage media having a system embodied thereon that, when executed, performs a method for managing a release of clinically related information, the system comprising:

an input interface that receives a request from a requesting party for the release of the clinically related information associated with a patient and validates a standing of the requesting party; and privacy management logic, wherein upon communicating with the input interface, the privacy management logic:

after the input interface receives the request, annotates a receipt status of the request in an access history database to create a privacy disclosure history for the patient, the privacy disclosure history being stored for a specified history-interval and being accessible through a privacy management user interface;

determines a privacy status of the patient;

validates the request based on the standing of the requesting party and a patient-specified time-interval and, if the request cannot be validated based on the standing of the requesting party and the patient specified time-interval, annotates a denial status of the request in the access history database;

generates a response to the request based on the privacy status of the patient;

extracts data from an electronic medical record associated with the patient, wherein the privacy status of the patient includes at least one recorded patient consent for the release of the clinically related information within the electronic medical record associated with the patient to the requesting party within the patient-specified time-interval, and wherein the at least one recorded patient consent permits release of only a portion of the clinically related information within the electronic medical record associated with the patient, the portion being less than a whole of the clinically related information within the electronic medical record associated with the patient and being-specified within the at least one recorded patient consent; and after extracting data from the electronic medical record associated with the patient, annotates a completion status of the request in the access history database.

2. A computer-storage medium according to claim 1, wherein the privacy management logic comprises at least a release manager, a privacy status manager, a request manager and a publishing manager.

3. A computer-storage medium according to claim 2, wherein the publishing manager extracts the data in response to the request.

4. A computer-storage medium according to claim 2, wherein the privacy status manger stores consent status information for the patient.

5. A computer-storage medium according to claim 2, wherein the request is received via the request manager.

6. A computer-storage medium according to claim 2, wherein the publishing manager, the privacy status manager, the release manager and the request manager are hosted in a client.

7. A computer-storage medium according to claim 1, wherein the privacy management logic receives a record of a hard copy request for release and generates the record of the hard copy request in electronic form.

8. A computer-storage medium according to claim 1, wherein the electronic medical record is stored in a clinical data store.

9. A method for managing a release of clinically related information, comprising:

receiving a request from a requesting party for the release of clinically related information associated with a patient and after receiving the request, annotating, via a first computing process, a receipt status of the request in an access history database, wherein the access history database provides a privacy disclosure history for the patient, the privacy disclosure history being stored for a specified history-interval and being accessible through a privacy management user interface;

validating, via a second computing process, a standing of the requesting party;

determining, via a third computing process, a privacy status of the patient, wherein the privacy status includes at least one recorded consent of the patient for the release of the clinically related information associated with the patient within an electronic medical record associated with the patient to the requesting party within a patient-specified time interval, wherein the at least one recorded consent of the patient permits the release of only a portion of the clinically related information within the electronic medical record associated with the patient, the portion being less than a whole of the clinically related information within the electronic medical record associated with the patient and being specified within the at least one recorded consent of the patient;

generating, via a fourth computing process, a response to the request based on the privacy status of the patient;

validating, via a fifth computing process, the request based on the standing of the requesting party and the patient-specified time-interval and if the request cannot be validated based on the standing of the requesting party and the patient-specified time-interval, annotating, via a sixth computing process, a denial status of the request in the access history database; and extracting, via a seventh computing process, data from the electronic medical record associated with the patient, after extracting the data from the electronic medical record associated with the patient, annotating, via eighth computing process, a completion status of the request in the access history database;

wherein each computing process is performed by one or more computing devices.

10. The method according to claim 9, wherein the privacy status comprises patient consent status information.

11. The method according to claim 9, further comprising receiving a record of a hard copy request for release, and generating the record of the hard copy request in electronic form.

12. A method for creating a set of clinically related data, selected from an electronic medical record associated with a patient and based upon privacy criteria associated with the patient, the method comprising:

receiving a request from a requesting party for a release of the set of clinically related information associated with the patient and after receiving the request, annotating, via a first computing process, a receipt status of the request in an access history database, wherein the access history database provides a privacy disclosure history for the patient, the privacy disclosure history being stored for a specified history-interval and being accessible through a privacy management user interface;

validating, via a second computing process, a standing of the requesting party;

determining, via a third computing process, a privacy status of the patient, wherein the privacy status includes at least one recorded consent of the patient for the release of the set of clinically related information within the electronic medical record associated with the patient to the requesting party within a patient-specified time-interval, and wherein the at least one recorded consent of the patient permits release of only a portion of the set of clinically related information within the electronic medical record associated with the patient, the portion being less than a whole of the set of clinically related information within the electronic medical record associated with the patient and being specified within the at least one recorded consent of the patient;

generating, via a fourth computing process, a response to the request based on the privacy status of the patient;

validating the request, via a fifth computing process, based on the standing of the requesting party and the patient-specified time-interval and if the request cannot be validated based on the standing of the requesting party and the patient-specified time-interval, annotating, via a sixth computing process, a denial status of the request in the access history database; and extracting, via a seventh computing process, the set of clinically related data from the electronic medical record associated with the patient, after extracting the set of clinically related data, annotating, via a eighth computing process, a completion status of the request in the access history database;

wherein each of the computing processes are performed by one or more computing devices.

13. The method for creating the set of clinically related data according to claim 12, wherein the privacy status comprises patient consent status information.

14. The method for creating the set of clinically related data according to claim 12, wherein the method further comprising recording a release event to the access history database upon validation of the request.

15. The method for creating the set of clinically related data according to claim 12, further comprising:

receiving a record of a hard copy request for the release; and generating the record of the hard copy request in electronic form.

* * * * *